US007201901B2

(12) United States Patent
Van Holten et al.

(10) Patent No.: US 7,201,901 B2
(45) Date of Patent: Apr. 10, 2007

(54) CAPTURE, CONCENTRATION AND QUANTITATION OF ABNORMAL PRION PROTEIN FROM BIOLOGICAL FLUIDS USING DEPTH FILTRATION

(75) Inventors: Robert W. Van Holten, Flemington, NJ (US); Stephen M. Autenrieth, Bernardsville, NJ (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 504 days.

(21) Appl. No.: 10/444,606

(22) Filed: May 23, 2003

(65) Prior Publication Data

US 2004/0033224 A1    Feb. 19, 2004

Related U.S. Application Data

(60) Provisional application No. 60/383,180, filed on May 23, 2002.

(51) Int. Cl.
*A61K 39/00*  (2006.01)
*A23L 1/28*   (2006.01)
*A23J 1/00*   (2006.01)

(52) U.S. Cl. .................... 424/140.1; 426/425; 530/419
(58) Field of Classification Search ............. 424/140.1; 426/425; 530/419
See application file for complete search history.

(56) References Cited

U.S. PATENT DOCUMENTS

| | | | |
|---|---|---|---|
| 2,390,074 A | 12/1945 | Cohn | |
| 3,449,314 A | 6/1969 | Pollack | |
| 3,916,026 A | 10/1975 | Stephan | |
| 4,021,540 A | 5/1977 | Pollack et al. | |
| 4,141,887 A | 2/1979 | Seafert | |
| 4,590,002 A | 5/1986 | Zolton et al. | |
| 4,859,340 A | 8/1989 | Hou et al. | |
| 4,880,913 A | 11/1989 | Doleschel et al. | |
| 5,115,101 A | 5/1992 | Bloom et al. | |
| 5,215,681 A | 6/1993 | Truong et al. | |
| 5,723,123 A | 3/1998 | Karges et al. | |
| 5,858,641 A | 1/1999 | Shanbrom | |
| 6,096,872 A | 8/2000 | Van Holten et al. | |
| 6,166,187 A | 12/2000 | Prusiner et al. | |
| 6,221,614 B1 | 4/2001 | Prusiner et al. | |
| 6,270,672 B1 | 8/2001 | Turecek et al. | |
| 6,916,419 B2 | 7/2005 | Prusiner et al. | |

FOREIGN PATENT DOCUMENTS

| WO | WO 96/00237 A1 | 1/1996 |
|---|---|---|
| WO | WO 98/08603 A1 | 3/1998 |
| WO | WO 00/43048 | 7/2000 |
| WO | WO 00/43782 A2 | 7/2000 |

OTHER PUBLICATIONS

Roberts, Peter L., "Value of Virus Filtration as a Method for Improving the Safety of Plasma Products", Vox Sang 1995;69;82-83.
DiLeo, Anthony J. et al., "Size Exclusion Removal of Model Mammalian Viruses Using a Unique Membrane System, Part 1: Membrane Qualification", Biologicals (1993)21, 275-286.
Tateishi, Jun et al., "Removal of Causative Agent of Cruetzfeldt-Jakob Disease (CJD) Through Membrane Filtration Method", (Original Contribution) (Membrane), 18(6), 357-362 (1993).
Burnouf, T., Value of Virus Filtration as a Mehod for Improving the Safety of Plasma Products, Vox San 1996;70:235-236.
Oncley, J.L. et al., The Separation of the Antibodies, Isoagglutinins, Prothrombin, Plasminogen and $\beta_1$-Lipoprotein into Subfractions of Human Plasma, Feb. 1949 vol. 71, pp. 541-550.
Bridonneau, P. et al., "Liquid Pasteurization of an Immunoglobulin Preparation without Stabilizer: Effects on its Biological and Biochemical Properties", Vox San 1996;70;203-209.
Tomasi, Thomas, Immunobiology, Current Knowledge of Basic Concepts in Immunology and Their Clinical Applications, The Gamma A Globulins: First Line of Defense, pp. 76-83.
Hardy, R.R., "Purification and characterization of monoclonal antibodies", Handbook of Experimental Immunology in Four Volumes.
Dortand's Illustrated Medical Dictionary, Immunodeficiency Disorders, Diseases, and syndromes.
Van Holten, R.W. et al., Incorporation of Viral Clearance Step into a Modified Cohen Fractionation, Transfusion, 1995-vol. 35, Supplement.
Physicians' Desk Reference MICRhoGAM.
PCT International Search Report, dated Sep. 3, 2004, for PCT Int'l. Appln. No. PCT/US03/16347.
Prusiner, S. B., "Prion Encephalopathies of Animals and Humans", *Developments in Biological Standardization*, 1993, 80: 31-34, S. Karger AG, Switzerland.
Turner, M. L., et al., "New-Variant Creutzfeldt-Jakob Disease: The Risk of Transmission by Blood Transfusion", *Blood Reviews*, , 1998, 12: 255-268, Churchill Livingstone, Edinburgh.
Burnouf, T., et al., "Reducing the Risk of Infection from Plasma Products: Specific Preventative Strategies", *Blood Reviews*, 2000, 14: 94-110, Harcourt Publishes Ltd.
Foster, P. R., "Assessment of the Potential of Plasma Fractionation Processes to Remove Causative Agents of Transmissible Spongiform Encephalopathy", Transfusion Medicine, 1999, 9: 3-14.
Lee, Douglas C., et al., "Monitoring Plasma Processing Steps With a Sensitive Western Blot Assay for the Detection of the Prion Protein", JVMEDH, 2000, 84(1), 77-89.

(Continued)

*Primary Examiner*—Susan Hoffman
*Assistant Examiner*—Randall Winston

(57) ABSTRACT

Methods for producing biological solutions such as immunoglobulins and in particular anti-D immunoglobulin substantially free of abnormal prion protein resulting therefrom. Specifically provided are methods for aggregation of prions and depth filtration of the biological solution to capture and remove abnormal and if desired, normal prion protein. The prion protein may then be eluted from the depth filter and filter washes and concentrated sufficient for detection at limits currently required by available assays.

1 Claim, 1 Drawing Sheet

OTHER PUBLICATIONS

Foster, Peter R., et al., "Studies on the Removal of Abnormal Prior Protein by Processes Used in the Manufacture of Human Plasma Products", Vox Sanguinis, 2000, 78: 86-95.

Lee, Douglas C., et al., "A Direct Relationship Between the Partitioning of the Pathogenic Prion Protein and the Transmissible Spongiform Encephalopathy Infectivity During the Purification of Plasma Proteins", Transfusion , 2001, 41(4), 449-455.

Cohn, E. J., et al., "Preparation and Properties of Serum and Plasma Proteins. IV. A System for the Separation into Fractions of the Proteins and Lipoprotein Components of Biological Tissues and Fluids", J. Am Chem. Soc., 1946, 68, 459.

Shaked, Gideon M., et al., "A Protease-Resistant Prion Protein Isoform Is Present in Urine of Animals and Humans Affected with Prion Diseases", J. Biol. Chem. , 2001, 276(34), 31479-31482.

Prusiner, Stanley B., et al., "Molecular Properties, Partial Purification, and Assay by Incubation Period Measurements of the Hamster Scrapie Agent", Biochemistry, 1980, 19, 4883-4891.

Winklhofer, Konstanze F., et al., "A Sensitive Filter Retention Assay for the Detection of $PrP^{sc}$ and the Screening of Anti-Prion Compounds", FEBS Letters 2001, 503: 41-45.

Wadsworth, J.D.F., et al., "Tissue Distribution of Protease Resistant Prion Protein in Variant Creutzfeldt-Jakob Disease Using a Highly Sensitive Immunoblotting Assay", Lancet, 2001, 358: 171-180.

Safar, Jiri, et al., "Eight Prion Strains Have $PrP^{sc}$ Molecules With Different Conformations", Nature Medicine, 1998, 4(10): 1157-1165.

MacGregor, I, "Prion Protein and Developments in its Detection", Transfusion Medicine, 2001, 11: 3-14.

Pocchiari, Maurizio, et al., "Combination Ultrafiltration and 6 $M$ Urea Treatment of Human Growth Hormone Effectively Minimizes Risk From Potential Creutzfeldt-Jakob Disease Virus Contamination", Horm. Res, 1991, 35: 161-166.

Gölker, C. F., et al., Reduction of the Infectivity of Scrapie Agent as a Model for BSE in the Manufacturing Process of Trasylok®, Biologicals, 1996, 24: 103-111.

Saborio, Gabriela P., et al., "Sensitive Detection of Pathological Prion Protein by Cyclic Amplification of Protein Misfolding", Nature, 2001, 411: 810-813.

Prowse, C. V., "Preliminary Assessment of Whole-Blood, Red-Cell and Platelet-Leucodepleting Filters for Possible Induction of Prion Release By Leucocyte Fragmentation During Room Temperature Processing", British Journal of Haematology, 1999, 106: 240-247.

"EMEA Expert Workshop on Human TSEs and Plasma-Derived Medicinal Products", The European Agency for the Evaluation of Medicinal Products *Evaluation of Medicines for Human Use*, CPMP/BWP/1244/00, 1-13, London, 2000.

Van Holten, Robert W., et al., "Removal of Prion Challenge From an Immune Globulin Preparation By Use of a Size-Exclusion Filter", Transfusion, 2002, 42: 999-1004.

Van Holten, Robert et al., "Evaluation of Depth Filtration to Remove Prion Challenge From an Immune Globulin Preparation", Vox Sanguinis, 2003, 85: 20-24.

CAPTURE, CONCENTRATION AND QUANTITATION OF ABNORMAL PRION PROTEIN FROM BIOLOGICAL FLUIDS USING DEPTH FILTRATION

The Application claims priority from U.S. Provisional Application 60/383,180, filed on May 23, 2002.

BACKGROUND OF THE INVENTION

Transmissible spongiform encephalopathies (TSEs) are a collection of neurodegenerative diseases characterized by progressive dementia, ataxia, amyloid plaque formation and spongiform degeneration in the central nervous system (CNS) (Prusiner, S. B., 1993, Dev. Biol. Stand. 80, 31–44). The causative agent in such diseases is now understood to be abnormal prion protein. The fundamental event in TSEs such as Creutzfeldt-Jakob disease (CJD) in humans, bovine spongiform encephalopathy (BSE) is cattle and scrapie in sheep is the conversion of the normal cellular prion protein $PrP^C$, into a pathogenic isoform, $PrP^{sc}$. Accumulation of $PrP^{sc}$ in the brain of prion-infected animals correlates with the rise in titer of infectious prions and is used as a diagnostic marker for prion diseases. In light of the threat of an interspecies transmission of BSE to humans, a large number of domestic animals must be tested for the presence of $PrP^{sc}$ in the brain or other suitable material. In the absence of covalent modifications that would allow a distinction between $PrP^{sc}$ and $PrP^C$, $PrP^{sc}$ is routinely detected in Proteinase K (PK)-treated homogenates by Western blotting or enzyme-linked immunosorbent assay (ELISA) utilizing the fact that $PrP^{sc}$ but not $PrP^c$ is partially protease resistant. Notably, these currently available assays do not take advantage of the fact that $PrP^{sc}$ forms aggregates. It is now believed that formation of detergent-resistant $PrP^{sc}$ aggregates is a general biochemical property of $PrP^{sc}$ even for rare prion strains where $PrP_{sc}$ is sensitive to proteolytic digestion. This aggregation occurs when the prions are exposed to an aggregation aid for example including a complexing agent.

The fatal human neurodegenerative disorder CJD has also been transmitted iatrogenically via a number of routes suggesting the possibility that the causative agent might also be transmitted via blood products. The identification of a new form of human TSE, named "variant" CJD (vCJD), confirmation of an association with the agent of bovine spongiform encephalopathy (BSE) and evidence that the distribution of the agent of vCJD in human tissues may differ from that of classical CJD suggests the existence of a theoretical risk that blood or blood products may transmit $PrP^{sc}$ (see Turner et al., Blood Reviews 1998; 12:255–68).

A number of blood products are prepared for medical use from pooled donations of human plasma including normal and specific immunoglobulins, coagulation factor concentrates and solutions of albumin. There is currently considerable concern about the possibility that biopharmaceutical products from human or animal sources may transmit TSEs. Human plasma proteins for parenteral administration inherently carry a risk for disease transmission. Current technology for plasma screening and process steps for the removal or inactivation of viruses has greatly improved the safety of these products, see Burnouf T, et al., Blood Reviews 2000; 14:94–110, in this regard. However, suitable screening tests have not yet been developed for abnormal $PrP^{sc}$, which are also extremely resistant to chemical and physical means of inactivation. To determine the probability of vCJD having been transmitted to patients by products derived from this plasma, it is necessary to determine the transmissibility of the $PrP^{sc}$ in clinically relevant circumstances, the extent to which procedures used for plasma fractionation were capable of eliminating the $PrP^{sc}$ from plasma products, and the extent to which the agent $PrP^{sc}$ can be detected in the biological product using available assays.

Human plasma is obtained from whole blood following removal of the larger cellular fractions. Recent studies performed by the plasma fractionation industry have demonstrated that process steps used in the manufacture of human plasma products may reduce $PrP^{sc}$ (see Foster P., Trans. Med. 1999, 9:3–14; Lee DC et al., J. Virol. Methods 2000, 84:77–89; Foster P. et al., Vox Sang 2000, 78:86–95, and Lee D. et al., Transfusion 2001, 41:449–55.) These process steps include Cohn fractionation, depth filtration and chromatography. Foster et al. (Vox Sang, supra.) demonstrated that depth filtration was effective in removing significant amounts of abnormal prion protein ($PrP^{sc}$) from both immunoglobulin and albumin.

There is therefore a need to develop methods of capture and removal of the abnormal infective prions from animal or human derived medicinal products or food products which are effective yet do not substantially degrade and/or remove the biological activity or food value of the product. Due to the limitations of the current methods of detection and quantitation of abnormal prions, there is an unmet need in ability to concentrate to above detection limits and thereafter detect and accurately quantitate the abnormal prion protein ($PrP^{sc}$) from the sample.

The instant invention is based on the surprising discovery that depth filtration of aqueous liquids containing biological products, such as for example a biologically active protein, with one or more depth filters having a pore size less than six microns, is surprisingly effective in removing abnormal infective prion proteins. More particularly, these inventors have made the surprising discovery that depth filtration of aqueous liquids containing biological products, such as for example a biologically active protein, with one or more depth filters having a pore size less than six microns, after treatment with an aggregation aid, is surprisingly effective in removing abnormal infective prion proteins.

The invention provides a method for the capture, removal, concentration and subsequent accurate quantitation of $PrP^{sc}$ associated with TSEs, when such TSEs are contained in biological or food products.

In particular, the invention provides a method for said capture, removal, concentration and subsequent accurate quantitation of $PrP^{sc}$ associated with TSEs, in biologicals that have been treated with one or more aggregation aids which results in aggregation of the $PrP^{sc}$ such that the $PrP^{sc}$ will be captured in and on a filter. Any method that results in such aggregation may be employed as an aggregation aid as contemplated herein. In particular it has been found that solvents such as for example alcohols may be employed. In the methods of the invention, an aggregation aid such as a solvent liquid that has been admixed with the biological or food product is passed through a filter formed of a matrix of cellulose fiber impregnated with diatomaceous earth or similar filter material which may be coated with a cationic resin having an average pore diameter of the filter ranging from 0.1 micron to 6 micron. Typically the filter may be a single use disposable filter.

In particular, the invention provides a method for the capture, removal, concentration and subsequent accurate quantitation of $PrP^{sc}$ associated with TSEs in biologicals that have been treated with one or more aggregation aids, for example solvent such as for example an alcohol, such as for example alcohol-fractionated immunoglobulin solutions, which comprises passing the solvent liquid containing the biological or food product through a depth filter formed of a matrix comprising solid particles of porous material and having a pore size providing a retention less than 6 μm. Typically the filter will be a single use disposable filter. The treatment with the aggregation aid(s) may be accomplished with the one or more aids admixed together or used in series.

By the terms "removal" or "capture" is meant the actual physical removal of the $PrP^{sc}$ from the liquid containing the desired protein. For practical purposes, the recovery of the desired protein in its original biological state should be substantially maintained at least to a level in excess of 50%, preferably 80%, more preferably >90%.

Using the methods of the invention, removal of the abnormal infective prion protein may be achieved to an extent of at least $10^{2.5}$, $10^3$, preferably $10^4$, more particularly >$10^5$.

Aside from removal of the infective $PrP^{sc}$ from the biological or food product, the invention also relates to the elution from the one or more filters and subsequent concentration of the captured and eluted $PrP^{sc}$ using an elution buffer which may comprise, for example, hypertonic solutions such as for example high salt solutions so the $PrP^{sc}$ may be accurately quantitated using available assays.

Thus, the instant invention provides for aggregation of prions followed by filtration for the purification of a biological or food solution, the elution of the prions from the filter and the concentration of the $PrP^{sc}$ so as to enable one skilled in the art to employ available assays to quantitate both total prion and $PrP^{sc}$ in a biological or food sample. The invention will further allow the rapid high-throughput testing of large numbers of samples for $PrP^{sc}$.

The invention also relates to the treated biological or food solution.

Since the source of human plasma is whole blood following removal of the larger cellular fractions, we therefore, in order to simulate the state expected of a TSE agent in plasma for fractionation, herein used as an inoculum a fraction of scrapie-infected hamster brain from which intact cells and larger fragments had been removed. TSE diseases are believed to be transmitted either by protease -K-resistant, conformationally abnormal prion protein ($PrP^{sc}$). We herein disclose an in vitro method of analysis to determine the distribution of hamster-adapted scrapie $PrP^{sc}$ as a marker for the partitioning behavior of vCJD.

TSE agents are highly resistant to inactivation, therefore reduction of any product-associated risk will be dependent on the physical removal of infective material during product manufacture. Process technologies used in the manufacture of plasma products include the separation of proteins by precipitation and chromatography with resultant protein solutions being clarified and sterilized by depth and membrane filtration procedures, respectively. Some of these technologies by their modification with the methods of this invention, may be capable of removing TSE agents from a product stream.

PrP protein was detected herein using a Western Blot with the monoclonal antibody 3F4 specific for hamster PrP. This antibody reacts with residues 109–112 PrP from only humans, hamsters and felines. Incubation with 3F4 antibody was at a concentration of 0.6 ug/ml for a minimum of 1 hour, after which excess antibody was washed away and the membranes incubated with a rabbit anti-mouse horseradish peroxidase conjugate (1:1000 dilution) for a minimum of 1 hour. After extensive washing with TTBS, the membranes were developed using enhanced chemiluminescence.

In the manufacture of RhoGAM® RHO(D) Immune Globulin (Human) by this Assignee, $PrP^{sc}$ was removed to the limit of detection during depth filtration steps that are also used in the manufacture of immunoglobulins.

Western blotting is a method used to identify and characterize $PrP^{sc}$. The $PrP^{sc}$ is isolated by extraction and is differentiated by its partial resistance to proteinase K digestion. The $PrP^{RES}$ ($PrP^{sc}$ resistant to proteinase digestion) is identified by the migration positions of the glycosylation forms and fragments. The sensitivity of this assay is approximately 3 logs less sensitive than the infectivity assay. This sensitivity issue is partially overcome by centrifuging the enzyme digested preparation, removing the supernatant and resuspending the prion material in a smaller volume, resulting in a concentration of the prion material. We have shown that the prions can be easily concentrated by filtering them through a filter after treatment with an aggregation aid, and later collected in a small volume by elution. This technique can be used on a large scale to remove prions from a product stream.

This procedure will have a major impact on the use of the Western blot and indeed any other prion detection assay, to determine the presence of $PrP^{sc}$ in a biological matrix. This invention allows the TSE material to be quantitatively concentrated quickly to allow for enhanced detection. When seeking to purify a biological, food or cosmetic solution of $PrP^{sc}$, this invention has the advantage in the ease in which the biological, food or cosmetic solution filters through the large nominal pore size of the filter.

The methods of the invention are useful for the treatment of biologicals, foods and cosmetics by removing, eluting and, further, quantitating $PrP^{sc}$, and depending on the aggregation aid(s) employed, $PrP^C$. Among the biologicals that can be so treated are blood and blood components such as whole blood, blood serum and plasma, urine, cerebrospinal fluid and blood-derived biological products such as antibodies and immunoglobulins. One such antibody is the IgG immunoglobulin known as monoclonal anti-D immunoglobulin or RhoGAM® Rho(D) Immune Globulin (Human). This polyclonal immunoglobulin is used in the prevention of hemolytic disease of newborn wherein the mother is injected with Rho(D) immunoglobulin of human origin. Such a product is RhoGAM®, available from the assignee hereof, and it operates by preventing the unimmunized Rho (D) negative mother from responding to Rho (D) antigen present on red cells and 'received' from an Rho(D) positive infant. Thus, by preventing anti-Rho (D) production by the mother, the subsequent Rho (D) positive infant of this mother is protected from hemolytic disease of the newborn. This successful product is currently produced by a Cohn alcohol fractionation type process.

RhoGAM® Rho(D) Immune Globulin (Human) was the first successful prophylactic use of specific antibody to achieve antibody mediated immune suppression. RhoGAM® is an IgG immunoglobulin solution containing anti-Rho(D) at a dose of 300 micrograms of anti-D activity per dose. RhoGAM® can be given to the nonimmunized, Rho(D) negative pregnant woman at the appropriate time prevent future disease in her Rho(D) positive offspring. The disease is called hemolytic disease of the newborn or more specifically, Rh-erythroblastosis fetalis.

A smaller dose of anti-Rho(D), MICRhoGAM® Rho(D) Immune Globulin (Human) Micro-Dose (50 micrograms of anti-Rho(D)) is also sold by the Assignee hereof for treatment of women who have abortions and miscarriages at twelve weeks gestation or earlier. While the full dose protects the recipient for up to 15 ml of Rho(D) positive red cells, the smaller dose provides protection up to 2.5 ml of Rho(D) positive red cells. RhoGAM® is used as antenatal prophylaxis at 26 to 28 weeks gestation. Other indications include threatened abortion at any stage of gestation with continuation of pregnancy, abortion or termination of pregnancy at or beyond 13 weeks gestation, abdominal trauma or genetic amniocentesis, chorionic villus sampling (CVS) and percutaneous umbilical blood sampling (PUBS).

Most immunoglobulin injectable materials approved for use by the FDA and Bureau of Biologics have been produced by the alcohol fractionation procedure developed by Dr. E. Cohn of Harvard during the 1940s and described in Cohn et al., J. Am. Chem. Soc. 68, 459 (1946), incorporated herein by reference. This procedure coupled with the careful selection of plasma negative for hepatitis infectivity, HIV, and other blood-borne pathogens determined by the most sensitive tests available. That the products produced by this procedure are indeed safe can easily be demonstrated by the millions of non-infected recipients of product. The inventors hereof have now found that the alcohol employed in the Cohn process referenced hereinabove is sufficient to act as an aggregation aid in that it causes sufficient numbers of $PrP^{sc}$ particles to aggregate, such that $PrP^{sc}$ can be removed to the limits of detection using the inventive depth filtration, and eluted and concentrated to a level sufficient for such detection.

The solvent composition employed has minimal effect on the IgG particle but sufficiently aggregates the $PrP^{sc}$ sufficient to enable it to be removed to below its level of detection using available assays.

It is therefore an object of this invention to provide a method for removal of $PrP^{sc}$ and if desired, $PrP^{C}$, from biological and food solutions using prion aggregation aids and membrane or depth filtration. Depth filtration is preferably used.

It is also an object of the invention to remove $PrP^{sc}$ and if desired, $PrP^{C}$, from protein-containing liquids, particularly those derived from human plasma, without unacceptable effects on the nature or biological activity of the proteins.

It is a further object of the invention to capture, concentrate and detect to accurate quantitation, $PrP^{sc}$ from any biological fluid using the methods disclosed herein.

It is an object of the instant invention to provide abnormal infective prion -cleared, pure immunoglobulin for injection. Such a substantially pure product is produced using the processing methods of the invention.

It is a further object of this invention to provide a manufacturable process for purifying immunoglobulins from abnormal infective prion which is reasonable in terms of temporal, square foot and protein yield requirements.

It is a further object of the invention to provide a depth filter which can be a single use filter and may be disposed of having removed $PrP^{sc}$ from the process stream.

It is a further object of this invention to provide a concentrated $PrP^{sc}$ solution, by elution of said prions from the depth filter and filter washes.

It is yet a further object of this invention to provide a rapid assay for the assessment of $PrP^{sc}$ in various biological materials including biological fluids and human blood and plasma-derived products. Use of such assays as, for example, the Western Blot, require sufficient levels of prions unavailable in non-prion-aggregated, non-filtered biological solutions. This method provides a practical method to capture, elute and concentrate prions so that they can be detected using currently available assays. Use of these novel capture and elution methods increases sensitivity about 3 logs, enabling reduction in the volumes needed to perform the detection assays.

SUMMARY OF THE INVENTION

The methods of this invention are used to produce immunoglobulin (preferably monoclonal) substantially purified of abnormal prion protein. The substantially purified immunoglobulin is for example monoclonal or polyclonal anti-D immunoglobulin, for example RhoGAM® or MICRhoGAM®. This immunoglobulin formulation comprises from about 4.0 to 6.0% immunoglobulin by weight, and from about 80 to 200 ppm polysorbate 80, more preferably about 5.0% immunoglobulin by weight, and about 130 ppm polysorbate 80.

The above referenced immunoglobulin formulation is made generally by the steps of fractionating human plasma using an aggregation aid such as for instance an alcohol, wherein the fractionation comprises a filtration step; resuspending the resulting Precipitate II; admixing the resuspended Precipitate II with a high ionic strength buffer containing an excipient; and performing nanofiltration on the immunoglobulin.

The alcohol is preferably methanol and the filtration step is performed on Supernatant III in the fractionation process, using a depth filter for instance a Cuno Zeta Plus 90S depth filter.

The methods disclose a process for the manufacture of anti-D antibody substantially purified of abnormal prion protein, including fractionating human plasma in the presence of an aggregation aid such as for instance an alcohol wherein the fractionation comprises a filtration step. The filtration step may employ a depth filter such as for instance a Cuno Zeta Plus 90S depth filter, having a pore size rating of from about 0.6 to 6 micron. The resultant supernatant, referred to in the process as "Supernatant III" is processed to form a precipitate (called in the method "Precipitate II"), which is then resuspended and admixed with processing aids and nanofiltration on the resulting anti-D antibody performed thereon. The processing aids may include a high ionic strength buffer and a non-ionic excipient, for example 150 mM NaCl-Glycine buffer and polysorbate 80.

Further disclosed herein is a process for the manufacture of biological product substantially purified of abnormal prion protein by admixing the biological product with an aggregation aid such as a solvent sufficient to form aggregated abnormal and normal prion protein; and filtering the thusly acquired admixture with a depth filter. The biological product is blood or blood product, cerebrospinal fluid, or urine. When the product is blood, the blood may first be clinically centrifuged and the red blood cells and platelets removed from the blood prior to admixing with the aggregation aid. After the filtering step, the red blood cells and platelets may be added back to the blood. The depth filter may include for example a Cuno Zeta Plus 90S depth filter. The aggregation aid may be a solvent such as for instance an alcohol, for instance ethanol or methanol at a concentration of from about 2% to about 100%.

Yet further disclosed herein is a method for quantitating abnormal prion protein in a biological solution. This method may comprise admixing the biological solution with an aggregation aid(s) such as a solvent sufficient to aggregate the abnormal prion protein, filtering the admixture with a depth filter, eluting the abnormal prion protein off the depth filter by washing the filter with an elution buffer, optionally concentrating the elution buffer by such method as centrifugation, and performing an assay for abnormal prion protein on the elution buffer. The biological solution may be blood or a blood product (for example an immunoglobulin), cerebrospinal fluid, or urine.

DETAILED DESCRIPTION OF THE INVENTION

Figure 1:
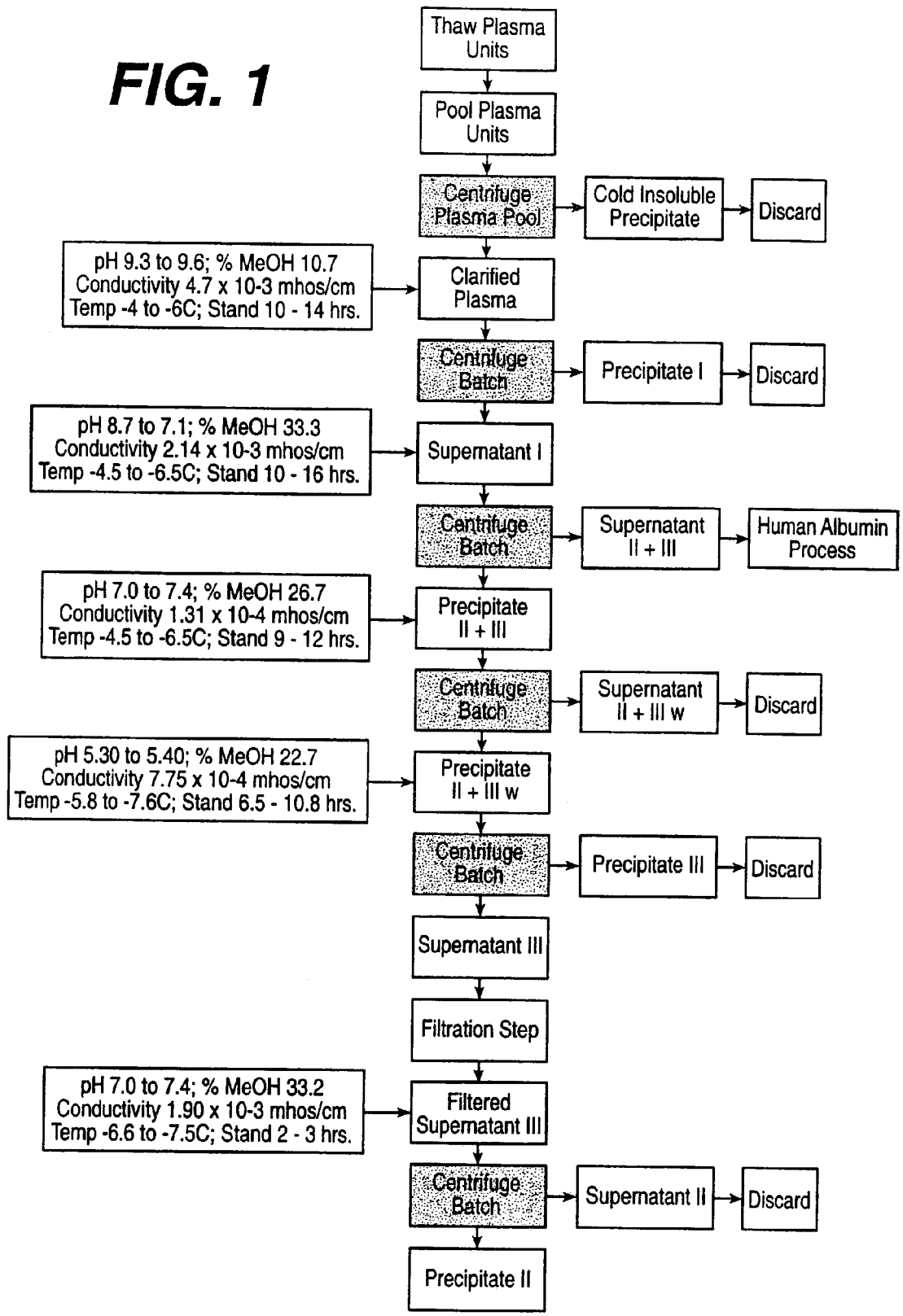
FIG. 1 is a flow sheet showing the process of fractionation of human plasma to obtain anti-Rh globulin. During this fractionation process the material may be filtered to capture prion protein.

The instant invention employs one or more aggregation aids to aggregate prion in a fluid, such that prion (normal and/or abnormal) may be eluted, captured, concentrated and detected. One class of aggregation aids will aggregate both abnormal infective prion ($PrP^{sc}$) as well as normal prions in a fluid, such as a biological fluid, which prion aggregates may then be removed, eluted, concentrated and either abnormal, normal or both types of prions accurately quantitated using the methods of the invention.

The invention further contemplates use of an aggregation aid which is a complexing agent, which agent aggregates either normal prions or abnormal prions, depending on the properties of the complexing agent. Such complexing agents include metal ions such as for example Cu2+, Ni, Zn, and Ag.

The invention allows a filter such as for example a depth filter to be used even with biological fluids comprising globular protein molecules such as for example an immunoglobulin or antibody, without appreciable yield loss and no significant change in immunoglobulin subclass, immunoglobulin aggregate level or immunoglobulin stability.

The methods of the invention yield a biological fluid substantially free of abnormal infective prions ($PrP^{sc}$) and if desired, normal prion ($PrP^{C}$). The methods of aggregation and filtration of the invention in fact can, when aggregation aids are properly selected to do so, ensure that all possible categories of prion, both normal and abnormal, are removed from the product.

The process is in particular applicable to the treatment of whole blood, blood components (e.g., serum, plasma), urine, CSF, or any biological such as for example liquids containing albumin, immunoglobulins (for example, IgG) and fragments thereof, blood coagulation factors such as Factor IX, thrombin, fibronectin, fibrinogen, Factor VIII and Factor II, VII, IX, and X and other proteins derived from plasma. It is also applicable to the treatment of plasma, Factor XI, Factor XIII, hemoglobin, alpha-2-macroglobulin, haptogobin, transferrin, apolipoproteins, protein C, protein S, C-1-esterase inhibitor, enzymes (for example, streptokinase), inter-alpha-trypsin inhibitor, growth hormones and Von Willebrand factor. Naturally occurring and recombinant analogues of the above may be treated. In addition, the invention is applicable to the treatment of other natural products including foods, drinks, cosmetics etc. It is also applicable to other non-plasma animal-derived products, such as heparin and hormones.

As stated herein, the biological fluids that can be processed using the methods of the present invention include blood and blood components such as whole blood and components thereof including blood serum and blood plasma, urine, cerebrospinal fluid, and any biological products such as for example antibodies and immunoglobulins.

The human plasma treated and filtered in the instant invention can be obtained by the fractionation methods of Cohn et al. (the "Cohn process"), referenced hereinabove, by batch or column exchange chromatography, or by affinity chromatography. In the method of producing immunoglobulin, particularly anti-D immunoglobulin such as RhoGAM Rho (D) Immune Globulin (Human), reference is made herein to commonly assigned U.S. Pat. No. 6,096,872, issued Aug. 1, 2000, to Van Holten et al., the contents of which are herein incorporated by reference.

Cohn, U.S. Pat. No. 2,390,074, the contents of which are herein incorporated by reference, discloses a method of fractionating blood by which gamma globulins are prepared. The gamma globulins prepared by the Cohn method contain 19 S globulin, plasminogen and lipids. While this gamma globulin is eminently suitable for prophylaxis against diseases such as measles and tetanus, the presence of the 19 S globulin, plasminogen and lipids are unnecessary contaminants and may decrease its effectiveness in preventing immunization to the Rh-factor on the fetal erythrocytes.

The substantially pure anti-Rh globulin manufactured by the validatable processes of the present invention is prepared from human plasma which contains albumin, plasminogen, alpha, beta and gamma globulins and various lipids. Specifically, the anti-Rh globulin of the invention is a gamma globulin.

The fractionation of human plasma to obtain anti-Rh globulin is carried out according to the methods of the aforementioned Cohn et al., as well as commonly-assigned U.S. Pat. No. 3,449,314 to Pollack et al., the teachings of which patents are hereby incorporated by reference herein. With reference to the accompanying flow sheet of FIG. 1, the ability to fractionate human plasma is dependent upon the solubility of the various components of the plasma. At each stage of the fractionation, the separation of the fraction and the ultimate removal of those components which are undesirable in the anti-Rh globulin are determined by the critical control of pH, temperature, concentration of the precipitant and the ionic strength of the system.

Various aggregation aids may be used in the aggregation of the prions resident in the biological fluids of the invention. There are a number of classes of aggregation aids that can be used, all working on the principle of changing the characteristics (e.g., the size) of the prion without aggregating or otherwise adversely affecting the milieu containing it.

It will be appreciated that some aggregation aids aggregate both abnormal and normal prion. Aggregation aids in this class include organic solvents of low dielectric constant such as acetone and alcohols, which are known to precipitate proteins and have been used in the fractionation of plasma. More particularly, the organic solvents utilized in the method of this invention include the various alcohols which are completely water-miscible and those that do not react with proteins, such as for example ethanol, methanol, isopropyl, isopropanol, n-propanol, isopropyl ether, ketones, aldehydes, etc., and acetone, and preferably methanol. Other similar aggregation aids in this class that may be used, to the extent they are compatible with the biological material being treated, include ammonium sulfate, caprylic acid, and the chemical agents trichloroacetic acid (TCA), dialdehydes, heteropoly acids, and lactate monohydrate $C_{18}H_{21}N_3O_4H_2O$.

It will further be appreciated that some aggregation aids will aggregate the abnormal prion thereby allowing it to be removed, while leaving the normal prion in its native state, and vice versa—this class of aggregation aids are the complexing agents. These complexing agents bind to the prion protein and include heteropolymolybdates, heteropolytungstates, sodium phosphotungstate (NaPTA) (all of which aggregate only abnormal prion), and the biological agents such as antibodies (monoclonal or polyclonal), the antibodies having action dependent upon their specificities, enzymes (such as for example plasminogen (which aggregates only abnormal prion) and peptides, peptides having selective action dependent upon their composition. A further aggregation aid which is a complexing agent includes the metal ion Cu2+, which aggregates normal prion. Other similar metal ions may include Ni, Zn, and Ag. These agents can be employed as a prion capture mechanism when bound to a substrate. In one embodiment it is contemplated that the complexing agents may be used in series, for instance, the ion Cu2+may be admixed with the biological solution and the normal prions removed by filtration, followed by admixing the resulting biological solution filtrate with the NaPTA to complex the abnormal prions, which may then be captured, eluted and concentrated and detected using known assay methods.

The aggregation aid methanol is preferred for prion removal from immunoglobulin solutions due to its comparatively lower toxicity and safer handling (e.g., explosion danger) than other organic solvents. When such solvents are used they are generally present in the admixture with the biological fluid in concentrations of about 2% to about 100% by volume of biological. The concentration of the solvent is dictated in the lower range by the minimum concentration required to aggregate the prions, and at the higher range by the integrity of the biological and the filter media.

It has now been found by these inventors that the inventive processing with aggregation aids such as those named hereinabove results in the aggregation of the prion (either or both $PrP^{sc}$ and $PrP^{C}$, depending on the aggregation aids and methods used in employing them) protein, and that using the methods of this invention, such aggregates can be removed using filtration. Then, using the inventive methods of filtration and later elution from the filter and the filter washes, and if desired, concentrating the eluate, the $PrP^{sc}$ can be obtained in concentrations sufficient to enable accurate quantitation. Using the methods of the invention it has been found that such treatment is sufficient to remove the $PrP^{sc}$ from the immunoglobulin formulation to below its detection limits. The sensitivity of assays used to detect such prion is increased by approximately 3 logs, enabling the reduction in volume and therefore increasing prion concentration in the sample.

For the $PrP^{sc}$ aggregation aspect of the invention, the aggregation aids that may be used are any that are found to precipitate abnormal infective prion protein fibrils while being compatible with the biological materials being treated, and compatible with the filter being used.

The filtration aspect of the invention may be carried out at any temperature that is appropriate to the biological materials being filtered, indeed the conditions for filtration are mandated by the biological, food or cosmetic product under filtration and not the conditions required to capture the prion material. In order to prevent denaturation of proteins during fractionation and filtration, the fractionation, where employed, and filtration may be preferably carried out at low temperatures. Since protein solubility is temperature dependent, the temperature chosen for each step of the fractionation must be the lowest possible which permits the desired separation and/or filtration in order to prevent denaturation. The pH conditions should be mandated by the liability of the biological product being purified.

The depth filters that may be used in the practice of the instant invention are those depth filters that are either charged or uncharged. Examples of depth filters that may be utilized include Celite (World Minerals, Lompoc, Calif.), Millipore filters 75DE and SA (Millipore Corporation, Bedford, Mass.), and Cuno 35P and Cuno Zeta Plus 90SP (Cuno Corporation, Meriden, Conn.).

Most preferable for use in the instant invention are the 47 mm Cuno Zeta Plus 90SP depth filter, along with the appropriate stainless steel filter housing, for small scale filtration work, and the 16 square foot cartridges used in manufacturing processes. Preferably the filter for use in the practice of the instant invention is a depth filter, however non-depth filters may be employed for removal of aggregated $PrP^{sc}$ as long as the filtration through these filters does not result in the clogging of said filters. Such alternate filters are for example membrane filters, charged or uncharged. Such filters include for example, the disposable syringe filters Swinex or Millex 25 mm PVDF syringe-driven filter units, 0.22 micron Opticap and Optiseal cartridges (Millipore Corporation, Bedford Mass.).

The pore size of the filters used in the practice of the removal and capture of $PrP^{sc}$ (and where desired, $PrP^{C}$) aggregates of the invention is relatively unimportant, however, the pore size can affect the recovery of the biological product being filtered. The pore size of the filter matrix is preferably in the range of 0.2 to 6 microns, particularly 0.6 to 1.5 microns. The pore size is defined in terms of the particle size of particles retained thereon. Typically particles of defined size such as dextrans or microorganisms are used for calibration purposes.

The pore size of the filtering units employed in the production of substantially pure, abnormal infective prion -free immunoglobulin products of the instant invention is less than about 6 μm, most preferably less than about 0.6 μm. However, any filter having a cutoff rating sufficient to reduce or eliminate abnormal infective prion from a proteinaceous solution can be employed in the processing methods of the invention. For example, for depth filters, Cuno Zeta Plus 90S filter pads (Cuno Corporation, Meriden, Conn.) may be employed, such unit having a molecular weight pore size rating of 0.1 to 5 micron.

Similarly, filter composition should have little effect on the ability of the filters to capture the aggregated $PrP^{sc}$, however, recovery of the prion material from said filters may require elution buffers such as high salt solutions or surfactants.

The filter material may comprise a depth filter which generally comprises a self binding matrix of cellulose, together with a solid porous particulate material such as Kieselguhr, perlite or diatomaceous earth.

The depth filter generally has a thickness in the range 1–10 mm, particularly 2–5 mm. The material used for the depth filter should have little or no effect in the desirable protein concerned. Acceptable depth filters include the Seitz KS80 filter of pore size 0.6 to 1.5 μm, the Seitz K200P, the Cuno Delipid Del 1 mini cartridge, effective filtration area 27 $cm^3$, Millipore filters, particularly the Millipore CP20, also including conventional ultrafilters such as Millipore PTHK polyethersulfone membrane, AMICON ym-100 regenerated cellulose ultrafiltration membrane, (Millipore Corporation, Bedford Mass.), PALL Filtron Omega VR, Pall Ultrapore VFDV50 (Pall Corporation, East Hills, N.Y.), along with other cartridge filters, such as the Asahi Planova regenerated cellulose cartridge filters, (Asahi, Tokyo Japan). Other filters that can be used are charged depth filters such as those of E. Begerow GmbH & Co., Langenlonsheim, Germany. However, the most preferable embodiments herein employ the Cuno Zeta Plus 90S filter pads, 47 mm filter.

The flow rate of the biological material through the filters are those rates suitable for ensuring proper filtration of the biological material while not compromising the integrity of the filter or, in the case of the biological material comprising large globular proteins, a rate that does not compromise the structure of the proteins so as to make the preparation unacceptable for its intended purpose. In the depth filtration of an immunoglobulin product for example, filtration rates range from about 0.01 to about 20 ml/minute, more preferably about 10 ml/minute, more preferably about 1 ml/minute.

The method may be carried out in the pH range of 4–10, preferably 5–9, more preferably 6–8. However, the pH range will be determined by that pH required to preserve the integrity of the biological being treated and the filter employed, and not by any limitation on the aggregation or filtration process itself.

The application of heat is unnecessary and the process can be carried out at substantially room temperature or below, in particular at the temperatures of −5 to +20° C., as suitable for maintaining the integrity of the biological and the filtering medium.

As stated hereinabove, an aspect of the instant invention is the treatment of the biological fluid with an aggregation aid such as for example a solvent sufficient to aggregate the prion contained therein so it may be captured by filtration and eluted in a concentration sufficient for detection using known methods such as for example, Western Blot. Some biological fluids will be so treated as a function of their production, for example, immunoglobulins which are treated with alcohol in the Cohn process. Where the biological fluid is not already so treated, it will be treated with a suitable aggregation aid such as those stated hereinabove so as to aggregate the prions contained therein. Such biological fluids are enumerated hereinabove and may include blood and components thereof, urine and cerebrospinal fluid, as well as immunoglobulins.

Following treatment of the biological with the aggregation aid, the filter pad is removed from its housing and prion eluted therefrom, concentrated if desired using a process such as centrifugation, and quantitated using available assays, all in accordance with remaining aspects of the invention, all herein described.

A protease resistant prion protein isoform is present in urine of animals and humans affected with prion disease. Shaked et al. (2001, J. Biol. Chem. 276 (34):31479–31482) discuss steps to isolate prions from urine. The process described in Shaked et al. requires 2–15 ml of a urine sample to be sedimented for 5 minutes at 3000 rpm and then dialyzed overnight in cellulose membrane tubes. Subsequently the urine samples were centrifuged at high speed (100,000×g) for 1 hour at 4° C.

The Shaked et al. procedure is time consuming and is limited by the amount of sample that can easily be concentrated. Disclosed herein is a procedure for accurately quantitating prions from a biological fluid such as urine, that may be accomplished in minutes and is not limited by volume. During prion filtration and elution from urine with the methods of the invention, up to 1 liter of urine volume may be filtered with a 47 mm Cuno filter. This volume difference allows for a magnitude increase in the concentrating capacity of the instant procedure compared to the current state of the art. See Example 9 herein.

When whole blood is used as the biological fluid in the invention, a quantity of it, for example 1 liter, may first be centrifuged under conditions suitable for separating the cellular component. The resulting plasma is admixed with an aggregation aid such as for example a quantity of methanol, for instance in a ratio of about 5 parts plasma to about 1 part methanol, to aggregate the prion material. The admixture is gently mixed on a rotary shaker for a period of time sufficient to aggregate the prions present, for example for about one (1) minute. The admixture is then passed through a filter for example a 47 mm Cuno Zeta Plus 90S filter. The material may then be eluted from the filter using an elution buffer as described herein, and the prions quantitated by any suitable assay, such as for example a Western Blot assay. If desired, the detection limit may be further improved by including a $PrP^{sc}$ sedimentation step. The samples were diluted and treated with Proteinase-K (PK) followed by AEBSF (4-(2-aminoethyl) benzensulfonyl fluoride) to inhibit proteinase activity. Following the PK treatment the sample is centrifuged at 20,000×g for 1 hour at 4° C. The pellet is then prepared for SDS Page.

When the biological material to be treated with prion aggregation aids is an immunoglobulin, the biological material will be so treated during the plasma fractionation process. With reference to FIG. 1 and Example 1 herein, plasma units are pooled and then under specified conditions are centrifuged and relevant portions are retained for further processing with the aggregation aid, in this case, preferably methanol. At the point of the fractionation wherein Supernatant III is obtained, the Supernatant III fraction is filtered using a membrane or depth filter, which filtration removes the aggregated prions that may have been contained therein. The aggregated prions captured thereby may be eluted from the filter and detected and quantitated using known assays.

The capture and elution procedures of the invention result in an increase in the detection limit of the assay by greater than 100 fold, now approaching the infectivity assay detection limit. Using methods currently available in the art, the infectivity assay can take months to yield results, dependent upon the species under study compared to hours for producing results using the methods of the invention.

Following aggregation of prions resident in biological fluid, whether by solvent or otherwise, the next steps are the prion (for example, $PrP^{sc}$) elution and recovery. In these steps the filter or filter pad(s) is/are removed and washed with elution buffer. One method is the placement of the pad(s) in a receptacle such as for example a petri dish, a beaker or similar suitable container, a suitable volume for example about 15 ml to about 100 ml of elution buffer added thereto, and the container placed on a rotary shaker at room temperature for about 25 minutes. The filter-bound $PrP^{sc}$ is thereby eluted therefrom via gentle washing with the elution buffer. Suitable elution buffers include any aqueous buffers, such as for example, hypertonic salt solutions such as for example 1.0–2.0M NaCl buffers, sodium acetate-methanol buffers at concentrations of 1.0M to about 2.0M.

If desired, the aggregated prions may be further concentrated by centrifugation or any procedure known in the art for achieving an increased concentration.

Given the theoretical possibility for prion contamination of blood products, it was especially important to elucidate the effectiveness of depth filtration and the mechanism for prion removal from an intermediate from immunoglobulin production RhoGAM® Ultra-Filtered Rho(D) Immune Globulin (Human). In accomplishing this goal, these inventors used scrapie brain homogenate (SBH) from scrapie-infected hamsters, as the source of the $PrP^{sc}$. In order to carry out such studies, the PrP$^{sc}$ "spike" was first treated with detergent to solubilize it, and sonicated to disrupt the fibrils. The spike was treated so as to make the PrP$^{sc}$ as small as possible so as to challenge the filtering system. The sonicated SBH was then sequentially 0.45, 0.22 and 0.1 micron membrane filtered to better define the size of the PrP$^{sc}$ spike prior to spiking. A previous study (Van Holten R, et al., Transfusion (submitted for publication)) had demonstrated that this treatment did not adversely effect the PrP$^{sc}$ and would additionally insure that the particles the depth filtration would remove would be closer in size to the individual fibrils associated with infection. A reduction in PrP$^{sc}$ after depth filtration could indicate that prion removal was due to the fibrils adsorbing to the positively charged filter media, rather than by mechanical straining. The addition of the spike into the IgG diluted in a phosphate buffer/methanol mixture resulted in flocculation of the material which resulted in a cloudy appearance.

A Cuno Zeta Plus SP charged depth filter was used to filter the RhoGAM® Rho(D) Immune Gamma Globulin (Human) that was spiked with the SBH. Upon filtration through a Zeta Plus SP filter the cloudiness was removed. A layer of white precipitate was observed on the filter post filtration. Upon Western blot analysis used to detect PrP$^{RES}$ the filter material was void of scrapie. With a 2.0M salt wash the prion material was recovered from the filter. The Western Blot results are shown herein in Table 1.

Two control runs were also performed. In the first run, the PrP$^{sc}$ spiked immunoglobulin intermediate was first filtered through a 0.22 µm filter to insure that the PrP$^{sc}$ did not aggregate to larger particles that could be removed by the depth filter through mechanical straining. In the second run, the sonicated and filtered SBH was spiked into Tris buffered saline (TBS) instead of the immunoglobulin intermediate, followed by the depth filtration.

The depth filter removed greater than four logs of PrP$^{sc}$ from the filtrate of the immunoglobulin. A significant portion of the PrP$^{sc}$ could be recovered from the immunoglobulin filtration by elution with high molarity NaCl solutions. The 0.22 µm prefiltration of the spiked Supernatant III removed all detectable PrP$^{sc}$ prior to depth filtration. Less than one log of PrP$^{sc}$ was removed from the buffer control by depth filtration. See Examples 6 and 7.

It was thus found that depth filtration removed PrP$^{sc}$ from the immunoglobulin by mechanical straining rather than by adsorption to the filter matrix. The immunoglobulin preparation caused the PrP$^{sc}$ to aggregate from particles <0.1 µm in size to particles >0.22 µm, probably as a result of the methanol in the immunoglobulin preparation. The depth filter failed to remove PrP$^{sc}$ from the buffer control sample.

In Example 3 herein, membrane filtration of the sonicated SBH was performed prior to depth filtration of the SBH spiked Supernatant III ("SupIII") in order to insure that the depth filter would see particles no greater than 0.1 micron in size. This would present the greatest challenge to the depth filter and would allow characterization of the mechanism of PrP$^{sc}$ removal. The SBH was first sonicated to break up the PrP$^{sc}$ aggregates and facilitate the membrane filtration. Despite the sonication, it was necessary to serially filter the SBH through progressively smaller filters (0.45 and 0.22 micron) to minimize clogging of the 0.1 micron filter.

The Cuno Zeta Plus 90SP depth filter utilizes two mechanisms for particle removal. Particles above the nominal pore size of approximately 0.1 micron are retained predominately by mechanical straining. Below 0.1 micron, particles with a negative charge are retained by electrokinetic adsorption to the positively charged filter media (U.S. Pat. No. 4,859,340).

Since particles greater than 0.1 micron had been removed from the SBH prior to addition to the Supernatant III and subsequent depth filtration, it appeared that the retention of the PrP$^{sc}$ by the depth filter was due to increase in particle size due to exposure to methanol. However, the charge capture mechanism of removal would be in effect when one departs from the isoelectric point of the prion being captured.

Examination of the depth filter after filtration of the SBH spiked SupIII and prior to elution with the 1.0M and 2.0M NaCl solutions revealed a small amount of material on the surface of the depth filter. This was believed to be a precipitate formed when the SBH was added to the SupIII, caused by the methanol present in the SupIII. In order to determine if this precipitate contained PrP$^{sc}$, a second run was performed where the SBH spiked SupIII was first pre-filtered through a 0.22 micron filter prior to depth filtration. The pre-filtration removed PrP$^{sc}$ to undetectable levels, indicating that in the prior run the PrP$^{sc}$ was removed by precipitation and mechanical straining, rather than by electrostatic adherence to the depth filter. Prusiner et al. (Biochemistry 1980; 19:4883–91) demonstrated that ethanol readily precipitated PrP$^{sc}$, so it is not surprising that the presence of the methanol used in this fractionation process would have the same effect.

In order to determine whether depth filtration would remove PrP$^{sc}$ in the absence of a precipitating alcohol, a control run was performed (see Example 4) where the PrP$^{sc}$ was spiked into an aqueous buffer and then depth filtered. The lack of removal of PrP$^{sc}$ from the buffer control indicated that the depth filter did not retain the protein, either by mechanical means (because the PrP$^{sc}$ had previously passed through a 0.1 micron filter) nor by electrostatic adherence.

These studies indicate that previous reports on the effectiveness of depth filtration to remove PrP$^{sc}$ may be misleading. Indeed, depth filtration does remove PrP$^{sc}$, not by the absorptive mechanism usually associated with depth filtration but by mechanical straining of the precipitated protein. The results of this study indicate that depth filtration alone is ineffective in removing PrP$^{sc}$. However, when used in conjunction with a prior precipitation step, depth filtration or membrane filtration can be an effective mechanism for abnormal prion protein removal from plasma fractions.

Any acceptable assay that detects prions may be used in the quantitation aspect of the invention. Among these assays are the ELISA, SDS-Page, Western Blot, EG & G Wallac, DELFIA, Prionics assay, Enfer ELC ELISA, CEA ELISA, Conformation-dependent assays, DELFIA, and capillary electrophoresis, to name a few, all of which are familiar to those having skill in the art.

The inventors hereof have employed the Western Blot to detect prion from the filtered and eluted biological fluid samples. Western blotting is a method of used to identify and characterize PrP$^{sc}$. The PrPsc is isolated by extraction and is differentiated by its partial resistance to proteinase K digestion. The PrP$^{RES}$ (PrP$^{sc}$ resistant to proteinase digestion) is identified by the migration positions of the glycosylation forms and fragments. The sensitivity of this assay is approximately 3 logs less sensitive than the infectivity assay. This sensitivity issue is partially overcome by centrifuging the preparation, removing the supernatant and resuspeding the prion material in a smaller volume, resulting in a concentration of the prion material. However, instead of spinning down large volumes of biological fluids such as for example body fluids, these inventors have shown that the prions can be captured by treating the biological fluid containing them with an aggregation aid, and then concentrating them by filtering them through a filter and later collecting them in a small volume by elution. This technique can be used on a large scale to remove prions from a product stream.

This procedure will have a major impact on the use of the Western blot to determine the presence of $PrP^{sc}$ in a biological matrix. This invention allows the TSE material to be quantitatively concentrated quickly to allow for enhanced detection. When seeking to purify a biological or food solution of $PrP^{sc}$ this invention has the advantage in the ease in which the biological or food solution and material filters through the large nominal pore size of the filter.

The standard Western Blot assay to confirm the specific capture of the prions relies on the captured material first being treated with Proteinase K, which digests all normal prion (PrPc) but does not markedly digest the abnormal prion ($PrP^{sc}$ or $PrP^{res}$). The digest is run in accordance with the methods of Lee et al., J Virol Methods 2000, 84:77–89, on the SDS gel and transblotted to a sheet of nitrocellulose or PVDF (polyvinylidene fluoride) membrane. The separated $PrP^{res}$ bands are then visualized using 3F4 or 6H4. Typical dilution is 1:2000 for 3F4 (stock 1 mg/ml) or 1:5000 for 6H4 (stock 2.5 mg/ml), 10 mL total volume in PBS Tween 20–5% nonfat milk buffer. The antibodies are detected with goat anti-mouse IgG-HRP conjugate (1:50,000 in the same buffer). Bands are detected with a HRP substrate usually be chemiluminescence and visualized after exposure to x-ray film. See Lee et al., supra.

Specific $PrP^{sc}$ monoclonal antibodies like 16A18 can specifically bind the $PrP^{sc}$ on magnetic beads (Dynal Tosyl activated), Dynal Biotech, Oslo, Norway), and such antibodies can be used to detect presence of $PrP^{sc}$ rather that Western Blot methods. Most of the antibodies in this family can capture $PrP^{sc}$ but detection has relied on the 3F4 or 6H4 in a Western Blot format as above.

Other methods to detect $PrP^{sc}$ include ELISA and SDS-Page and other generally accepted detection methods as disclosed hereinabove.

In the case where the $PrP^{sc}$ material is captured on a filter such as for example a sterilizing filter, which filter specifically binds prion such as with prion-specific antibody, Western Blot methods need not be employed to detect the $PrP^{sc}$. Rather, a prion-specific antibody such as a monoclonal could be employed to detect and quantitate the prion. Such an antibody includes the generic prion antibodies 6H4 or 3F4, which recognize both normal ($PrP^c$) and abnormal ($PrP^{sc}$ and $PrP^{res}$) prions. If the membrane binds all forms of prion, the relative amount of $PrP^{sc}$ would be very low (for instance less than about 1% of prion present). Specific monoclonals for abnormal prions, such as for example 16A18 or 12A5, could be used to detect $PrP^{sc}$ in the case where the membrane binds all forms (normal and abnormal) of prions. Using such monoclonals it should be possible to detect $PrP^{sc}$ if the signal could be amplified, if necessary, using chemiluminescence substrates or polyHRP conjugates.

The inventive methods disclosed herein results in an increase in the detection limit of the assay by greater than 100 fold, now approaching the infectivity assay detection limit. Using current methods available in the art, the infectivity assay can take months to yield results, dependent upon the species under study. These inventors have also shown that the assay can be simplified by detecting the presence of abnormal prion on the membrane surface not requiring elution.

In the use of the inventive methods of $PrP^{sc}$ aggregation and removal with an immunoglobulin, and in particular in the manufacture of an anti-D immunoglobulin, specifically RhoGAM Rho(D) Immune Globulin (Human), and referring to the flowsheet of FIG. 1 and the methods of Cohn et al., J. Am. Chem. Soc., Vol. 68, pages 459–475, the fractionation proceeds from whole human plasma. The plasma is cooled to about 1° C. and is then centrifuged to separate a cold insoluble precipitate from a supernatant. The supernatant is further fractionated to yield Precipitate I and Supernatant I. Precipitate I which consists principally of fibrinogen is discarded. Supernatant I is further fractionated to yield Supernatant II+III and Precipitate II+III. Supernatant II+III, which is discarded, contains alpha and beta globulin and lipids. Precipitate II+III consists principally of beta and gamma globulins and isoagglutinins, but also contains prothrombin, plasminogen, cholesterol and other lipids. Precipitate II+III, upon further fractionation yields Supernatant II+III W and Precipitate II+IIIW. The beta globulin, cholesterol and other lipids are largely removed in Supernatant II+III W which is discarded. Precipitate II+III W consists principally of gamma globulins, isoagglutinins, plasminogen and prothrombin and some beta globulin, cholesterol and other lipids. Upon further fractionation, Precipitate II+III W yields Supernatant III+Precipitate III. Precipitate III, which is discarded, contains isoagglutinins, plasminogen and prothrombin. Supernatant III consists principally of gamma globulins and minor amounts of fibrinogen and lipids. The final step of the fractionation yields Precipitate II which is essentially pure gamma G globulin. Precipitate II prepared by the process of the invention is an anti-Rh gamma globulin.

In the preferred methods of the invention, the immunoglobulin starting material for resuspension is the Precipitate II paste from the modified Cohn process. Lyophilized precipitate II paste may be used if the protein is lyophilized in the presence of excipient such as those contemplated by U.S. Pat. No. 6,096,872. The filtration process of the invention to capture prions in this case has preferably already been performed in the fractionation of Precipitate II; with reference to the above and to FIG. 1, the filtration of the Immunoglobulin leading to the capture of prions is performed before Precipitate II is obtained, after obtaining Supernatant III, or, most preferably, between Supernatant III and Filtered Supernatant III, as shown. Such treatment of material with the aggregation aid methanol, and at a ratio of about 4 to about 1 MeOH: Supernatant III aggregates prion in the Supernatant III, which aggregates can then be removed using further methods of the invention. The filtration steps allowing the prion capture of the invention may also be done on finished immunoglobulin product. However, treatment with aggregation aid and filtration could also be performed as the final stage of product processing, so long as the treatment and filtration at that stage do not interfere with the biological activity or otherwise compromise the final product.

The mode of administration of the preparations of the invention may determine the sites and/or cells in the organism to which the compound(s) will be delivered. The compounds purified by the methods of the invention can be administered alone but will generally be administered in admixture with a pharmaceutical carrier or diluent selected with regard to the intended route of administration and standard pharmaceutical practice. The preparations may be injected parenterally, for example, intra-arterially or intravenously. The preparations may also be delivered via oral, subcutaneous, or intramuscular routes. For parenteral administration, they can be used, for example, in the form of a sterile, aqueous solution which may contain other solutes, for example, enough salts or glucose to make the solution isotonic.

For the oral mode of administration, the purified compositions of the invention can be used in the form of tablets, capsules, lozenges, powders, syrups, elixirs, aqueous solutions and suspensions and the like. In the case of tablets, carriers which can be used include lactose, sodium citrate, and salts of phosphoric acid. Various disintegrants such as starch, and lubricating agents such as magnesium stearate are commonly used in tablets. For administration in capsule form, useful diluents are lactose and high molecular weight polyethylene glycols. When aqueous solutions are required for oral use, certain sweetening and/or flavoring agents can be added.

The substantially pure preparations of the present invention may be administered to a subject such as a mammal, including humans. For administration in the treatment of afflictions, the prescribing physician or veterinarian will ultimately determine the appropriate dose for a given human or animal subject, and this can be expected to vary according to the weight, age, and response of the individual as well as the nature and severity of the individual's symptoms.

In the case of the substantially pure anti-D immunoglobulin of the invention, the per-dose dosage will range from about 300 ug for RhoGAM® and about 50 ug for MICRhoGAM®, each of which are administered in accordance with the guidelines and for the purposes discussed hereinabove and in the respective product literature. Each of the products mentioned above can also be multi-dosed, for a total delivery to be determined by the treating physician.

The prion-free preparations of the invention may include biologicals, medicaments, foodstuffs and feeds, and the methods of the invention may be used in the processing of same.

Throughout this application, various patents and papers are referenced. The disclosures thereof in their entireties are hereby incorporated by reference into this application in order to more fully describe the state of the art as known to those skilled therein as of the date of the invention described and claimed herein.

The following examples are provided for the purposes of illustration only and are not to be viewed as a limitation of the scope of the invention.

EXAMPLES

Example 1

Production of Rho(D) Immune Globulin Precipitate II using Aggregation Aid

This Example describes a process for the fractionation of human plasma to obtain Precipitate II to be used in the production of Rho(D) immune globulin.

Plasma units (anti-D) (a total of approximately 943 L) were stored at 2° C. to 8° C. for four days to allow thawing. The units were pooled in a stainless steel water-jacketed tank through which water at 5–10° C. circulates. The pooled plasma was stirred for thirty (30) minutes at 1–3° C. The plasma was then centrifuged in a continuous flow centrifuge feeding at a rate of 1000 mL/minute. The cold insoluble supernatant (centrifuged plasma) was collected in a stainless steel jacketed tank and stirred until a homogeneous mixture was obtained. The batch volume at this point was 905 L of supernatant (clarified plasma).

The pH of the entire batch of supernatant was adjusted to pH 9.45 using 2.172 L of 5.0N NaOH. Methanol (71%), 160.185 L was added to the pH adjusted batch, which was at −5.3° C. pH was 9.37. The batch was allowed to stand for 13.5 hours at −5.2° C. Final volume was 1067.357 L.

The batch was centrifuged in a continuous flow centrifuge feeding at a rate of 1000 ml/minute at −5.8° C. Supernatant I was collected in a stainless steel jacketed tank, and well mixed. Precipitate I was discarded as medical waste. Supernatant I was pH adjusted by adding 3.132 L of conc. sodium acetate buffer, pH 4.0 and 627.444 L of 71% methanol. The batch temperature was −5.5° C. and the pH was 6.75. The batch was allowed to stand 14 hours.

The batch was centrifuged in a continuous flow centrifuge feeding at a rate of 1000 ml/minute at −5.5° C. Precipitate II+III was transferred into a stainless steel pot; 40.220 KG net weight was collected; this net weight Precipitate II+III was resuspended in two volumes (L) (80.440 L) of Water for Injection, U.S.P. at +1.1° C. and stirred for 45 minutes until a uniform suspension was obtained. Three volumes (120.660 L of 0.0187M disodium phosphate was added and stirred at 2.1° C. for 30 minutes.

In a stainless steel jacketed tank, 19 volumes (764.180 L) of Water for Injection, U.S.P. was cooled to 1.0° C. Using a high capacity transfer pump, the batch was slowly combined with the 19 volumes of Water for Injection, U.S.P., and was stirred for 30 minutes.

A volume of 71% methanol was adjusted to equal 15 times the weight of the Precipitate II+III. This methanol (603.300 L) was cooled to −14° C. and using a stainless steel Sparger device and a metering pump, the methanol was added to the batch while gradually lowering the temperature to −5.5° C. The batch was stirred for 1 hour after completion of the methanol addition. pH was 7.23. The batch was allowed to stand for 10 hours 20 minutes.

Precipitate III was formed via centrifugation of the batch in a continuous flow centrifuge feeding at a rate of 500 mL/minute at −5.8° C. The Precipitate II+III w was transferred from the bowls into a stainless steel pot; the net weight was 22.760 kg.

The Precipitate II+III w was resuspended in two volumes (L) (45.520 L) of Water for Injection, U.S.P. at +1.3° C. and stirred for 45 minutes until a uniform suspension was obtained. Two volumes (45.520 L) of 0.175M sodium acetate was added and stirred at 1.4° C. for 30 minutes. The pH of the entire batch was adjusted by addition of 0.489 L of sodium acetate buffer, pH 4.0 in 22.760 L Water For Injection U.S.P. (total volume 137.049 L) to the batch and stirred for 1 hour at 1.5° C. pH was 5.38. In a stainless steel jacketed tank, 13.5 volumes (307.260 L) water for Injection U.S.P. was cooled to +2.5° C. with stirring. Using a high capacity transfer pump, the batch was combined with the Water for Injection, total calculated volume was 444.309 L. NaCl (6.168 L of 1.33M) was added to the 22.760 Kg of Precipitate II+III, and was stirred for 30 minutes.

A volume of 71% methanol was adjusted to equal 8.78 times the weight of the Precipitate II+III w. This methanol (199.833 L) was cooled to −10.5° C. and using a stainless steel Sparger device and a metering pump, the methanol was added to the batch while gradually lowering the temperature to −6.6° C. The batch was stirred for 1 hour after completion of the methanol addition. pH was 5.38. The batch was allowed to stand for 8 hours 30 minutes at −6.3° C.

Formation of Precipitate III proceeded as follows:

The batch was centrifuged in a continuous flow centrifuge feeding at a feeding rate of 500 mL/minute at −6.3° C. The Supernatant III was collected in a stainless steel tank. The Precipitate III was discarded as blood waste.

The filtration of the Supernatant III proceeded as follows: The CUNO filter 90SP housing including (4) 16 sq. ft. cartridges, was assembled in accordance with manufacturer's instruction. Sodium acetate-methanol buffer (320 L) was cooled to −6.5° C., and was filtered through the filter cartridges over 55 minutes. The sodium acetate-Methanol Buffer wash solution was blown completely out of the filter cartridge before proceeding. The batch was filtered using the Cuno filter 90SP in accordance with good manufacturing practice and employing manufacturer's instructions. When the entire volume of Supernatant III was filtered, the pressure in the filter housing was released. Volume of filtered Supernatant III was 622 L, and was stirred at moderate speed. NaCl (1.33M, 23.387 mL) was added to Supernatant III slowly and stirred for 30 minutes at 6.5° C. pH was 5.38, and adjusted to 7.10 with 4.840 L of 1.0 M sodium bicarbonate and mixing for 30 minutes. Methanol (100%) equal to 0.166 times the volume of Supernatant III (103.252 L) was added to the Supernatant III using a Sparger device and a metering pump and the batch stirred vigorously. PH was 7.3.

Fractionation of Precipitate II was performed as follows: The batch was centrifuged in a continuous flow centrifuge feeding at a rate of 500 mL/minute at −6.3° C. and the supernatant discarded. Dry nitrogen was used to blow out the feed lines and dry spun for 15 minutes. The Precipitate II (7,420 g) was transferred from the centrifuge bowls into a tared, stainless steel pot and stored at −22.1° C. This material was used in the viral clearance process in accordance with the methods of co-assigned U.S. Patent to Van Holten et al., U.S. Pat. No. 6,096,872 issued Aug. 1, 2000.

Example 2

Elution and Detection of Prions from Example 1

The prions collected on the Cuno depth filter used to filter the Supernatant III obtained by the methods of Example 1 hereinabove are eluted, quantitated and detected using the methods of Example 3 hereinbelow.

In particular, the Cuno depth filter pad used in Example 1 is removed from the filter housing and placed in a petri dish with 45 ml of 1.0M NaCl (elution buffer). The petri dish is placed on a rotary shaker and swirled gently for about 20–30 minutes. The filter is removed and similarly washed a second time with 45 mL 10 of 2.0M NaCl (elution buffer) for 20–30 minutes.

Western Blot analysis of PrP$^{sc}$ on the eluate is performed on eluate from the 1.0M NaCl elution buffer and a second Western Blot performed separately on the eluate from the 2.0M NaCl elution, both in accordance with the Western Blot methods of Example 3.

Example 3

Removal and Quantitation of PrP$^{sc}$ from Immunoglobulin Preparation

Supernatant III (SupIII) (190 mL) containing anti-D was obtained from a full-scale (approx. 450 Liters) modified Cohn-Oncley fractionation (Ortho-Clinical Diagnostics, Raritan N.J.) (See Example 1 hereinabove). The SupIII was stored at −70° C. and thawed at 25° C. just prior to the addition of the scrapie brain homogenate (SBH), then equilibrated at a temperature of at −5.5 to −7.5° C.

Brain Homogenate

Scrapie brain homogenate (10%) was prepared using brain from hamsters infected with 263K hamster-adapted agent. Frozen brains (approx. 3–20 as ~0.5 grams per brain) were thawed on ice, then homogenized in nine volumes of Tris buffered saline, pH 8.0. The homogenate was clarified by centrifugation at 1200 r.c.f. at 2–80° C. for 20 minutes. One percent (1%) lysolecithin was added to the supernatant to a final concentration of 0.1% (w/v). This material was stored at −70° C. until use. Prior to use, the SBH was thawed in a room temperature water bath, then cup horn-sonicated (Misonix Sonicator XL2020 with cup horn, (Heat Systems, Farmingdale, N.Y.) for approximately two minutes per milliliter until the solution turned from turbid to translucent. The treated homogenate was then serially filtered through Millex® 25 mm PVDF syringe-driven filter units, (Millipore Corporation) 0.45/0.22/0.1 micron filters, which further clarified the material. The Supernatant III (SupIII) (200 mL) from the Cohn fractionation process was spiked with the filtered SBH (1:51 dilution). The second run was filtered through a 0.22 micron filter just prior to the start of the depth filtration to remove any aggregates that may have formed in the mixture (see Example 5). Samples of SHB were sampled for Western blot evaluation prior to treatment and after sonication and filtration.

Filtration

A 47 mm CUNO Zeta Plus 90SP filter pad (Cuno Corporation, Meridan Conn.) was placed in its stainless steel filter housing. A peristaltic pump was used to control the flow rate of the filtration to a rate of about 1 ml/min. The entire filter housing was placed in an insulated sodium chloride ice bath to cool the filter to approx. −5.5 to −7.5° C. Sodium acetate-methanol buffer (80 ml of 0.01N sodium acetate methanol buffer, 22.7% MeOH at −5.5 to −7.5° C. was used to wash the filter. The SBH-spiked SupIII (180 ml) at −5.5 to −7.5° C was filtered through the CUNO filter at a flow rate of 1.0 mL/minute. Aliquots of filtrate were collected at the beginning (75 ml), middle (75 ml) and end (30 ml) of the filtration. The pressure of the system was monitored during the entire filtration and was about 2 psi.

Elution of PrP$^{sc}$ from Filter

After filtration, the filter pad was removed from the filter housing and placed, rough side up, into a beaker and washed with 45 mL of 1.0M NaCl elution buffer for 20–30 minutes by gently swirling on a rotary shaker. The filter was removed and washed a second time with 45 mL of 2.0M NaCl for 20–30 minutes with gentle swirling on the rotary shaker. It would be possible to further concentrate the PrP$^{sc}$ by centrifugation at 100,000×g for about 1 hr. at 4 degrees C., however this was not necessary as it was sufficiently concentrated for Western Blot analysis as shown in Table 1.

A second run was identical to the first, except that the SupIII spiked with SBH was first pre-filtered through a Millex 0.22 micron filter.

A control run was performed, cooling the filter apparatus to 0° C. and washing the depth filter pad with 80 mL of TBS. TBS (180 mL) spiked with filtered SBH (1:51 dilution) was filtered under the same flow rates as above, followed by the filter washes. See Example 4.

Western Blot analysis of PrP$^{sc}$ on the eluate was performed on eluate from the 1.0M NaCl elution buffer and a second Western Blot performed on the eluate from the 2.0M NaCl elution, both in accordance with the Western Blot methods hereinbelow.

With reference to Table 1, data is shown wherein PrP$^{sc}$ is present as having been eluted from the filter after both elutions.

Western Blot

Sample Preparation

Sample preparation and assay methodology was performed in accordance with Lee et al., J Virol Methods 2000; 84:77–89. Samples were treated in a proteinase K digestion step that is used to differentiate the PrP$^c$ from the PrP$^{sc}$. Following the proteinase K treatment the samples were centrifuged at 20,000 r.c.f. for 1 hour at 4° C. The pellets were resuspended in 10 µl each of 2× sodium dodecyl sulfate (SDS) sample buffer and heated at 100° C. for five minutes. Half-log serial dilutions were prepared prior to loading onto gels for the detection of the PrP$^{RES}$ by Western blot, all in accordance with Lee et al. (supra)

Assay

Samples were assayed according to the method of Lee et al., supra. Each sample was electrophoresed on a 12% SDS-Tris-glycine polyacrylamide gel for 60 minutes at 125 constant volts. Gels were transferred to nitrocellulose membranes for 60 minutes at 125 constant mA, then soaked in TBS and blocked for 60 minutes in 5% non-fat milk. Following transfer and blocking the membrane was incubated in 3F4 monoclonal antibody. After washing, the membrane was exposed to an alkaline phosphatase-conjugated anti-mouse IgG secondary antibody. The blot was then soaked in CDP-Star plus NitroBlock II, and then exposed to Kodak XAR-2 film. A valid test was determined by the positive control exhibiting banding at 33 kDa mark. Two smaller less intense bands than the 33 kDa band are also typically observed. This triplet of bands is typical Western blot image for PrP$^{RES}$ (Lee et al, supra.).

Results

Sonication and serial membrane filtration removed all turbidity from the SBH. The subsequent depth filtration of the SBH spiked immunoglobulin preparation reduced the PrP$^{sc}$ concentration in the filtrate to a level below the limits of detection of the Western blot assay (Table 1) A significant amount of the PrP$^{sc}$ was recovered from the filter pad by elution with high salt solutions. Filtration of the SBH spiked SupIII through a 0.22 micron filter prior to depth filtration removed PrP$^{sc}$ to undetectable levels. The depth filtration of the SBH spiked into the buffer control removed little or no PrP$^{sc}$.

In Example 3 herein, membrane filtration of the sonicated SBH was performed prior to depth filtration of the SBH spiked SupIII in order to insure that the depth filter would see particles no greater than 0.1 micron in size. This would present the greatest challenge to the depth filter and would allow characterization of the mechanism of PrP$^{sc}$ removal. The SBH was first sonicated to break up the PrP$^{sc}$ aggregates and facilitate the membrane filtration. Despite the sonication, it was necessary to serially filter the SBH through progressively smaller filters (0.45 and 0.22 micron) to minimize clogging of the 0.1 micron filter.

Examination of the depth filter after filtration of the SBH spiked SupIII and prior to elution with the 1.0M and 2.0M NaCl solutions revealed a small amount of material on the surface of the depth filter. This was believed to be a precipitate formed when the SBH was added to the SupIII, caused by the methanol present in the SupIII. In order to determine if this precipitate contained PrP$^{sc}$, a second run was performed where the SBH spiked SupIII was first pre-filtered through a 0.22 micron filter prior to depth filtration. See Example 6. The pre-filtration removed PrP$^{sc}$ to undetectable levels, indicating that in the prior run the PrP$^{sc}$ was removed by precipitation and mechanical straining, rather than by adsorption to the depth filter.

TABLE 1

Determination of PrP$^{SC}$ by Western blot assay in an Immune Globulin preparation spiked with scrapie brain homogenate (SBH)

| Sample Name | Total Log$_{10}$ (prion unit) Reduction | Mass Balance | Log$_{10}$ Factor* |
|---|---|---|---|
| Depth Filtration of SBH spiked SupIII | | | |
| Spiked Load | 6.9 | 100% | >5.2 |
| Early Filtrate | <2.7 | 0% | |
| Middle Filtrate | <2.1 | 0% | |
| Late Filtrate | <2.1 | 0% | |
| Salt Strip (1 M) | 5.2 | 32% | |
| Salt Strip (2 M) | 5.0 | 1% | |
| Depth Filtration of SBH spiked SupIII with prior 0.22 µm filtration | | | |
| Spiked Load | 7.1 | 100% | >3.0 |
| Spiked Load II (0.22 µm filtered)† | <4.1 | 0% 0% | |
| Early Filtrate | <2.7 | 0% | |
| Middle Filtrate | <2.1 | 0% | |
| Late Filtrate | <2.0 | 0% | |
| Salt Strip (1 M) | 3.2 | 0% | |
| Salt Strip (2 M) | <3.5 | 0% | |
| Depth Filtration of SBH spiked TBS | | | |
| Spiked Load | 7.0 | 100% | 0.8 |
| Early Filtrate | 6.2 | 16% | |
| Middle Filtrate | 6.7 | 50% | |
| Late Filtrate | 6.0 | 11% | |
| Salt Strip (1 M) | 4.5 | 0.3% | |
| Salt Strip (2 M) | 4.5 | 0.3% | |

*Log$_{10}$ Reduction Factor is the difference between the PrP$^{RES}$ in the Spiked Load II compared to the Filtrate.
†Spiked Load II is the SBH spiked immune globulin (i.e. Spiked Load I) that was 0.22 micron filtered to remove any potential aggregates formed with the addition of the SBH to the IgG.
"<" indicates a maximum value; no PrP$^{RES}$ was detected in any of the filtrate samples.

Example 4

Control

In order to determine whether depth filtration would remove Prp$^{sc}$ in the absence of a precipitating alcohol, a control run was performed where the PrP$^{sc}$ was spiked into an aqueous buffer and then depth filtered.

The materials and procedures of Example 3 were repeated wherein the same concentration and volume (3.6 ml) of SBH was spiked into 180 ml of 0.1 M Tris Buffered Saline (TBS). The lack of removal of PrP$^{sc}$ from the buffer control indicated that the depth filter did not retain the protein, either by mechanical means (because the PrP$^{sc}$ had previously passed through a 0.1 micron filter) nor by electrokinetic adsorption. See Table 1.

These data indicate that previous reports on the effectiveness of depth filtration to remove PrP$^{sc}$ may be misleading. Indeed, depth filtration does remove PrP$^{sc}$, not by the absorptive mechanism usually associated with depth filtration but by mechanical straining of the precipitated protein. The results of this study indicate that depth filtration alone is ineffective in removing PrP$^{sc}$. However, when used in conjunction with a prior precipitation step, depth filtration or membrane filtration can be an effective mechanism for abnormal prion protein removal from plasma fractions.

Example 5

Elution of PrP$^{sc}$ from Filter

The filter pad used in Example 3 was removed from the filter housing and placed in a petri dish with 45 ml of 1.0M NaCl (elution buffer). The petri dish was placed on a rotary shaker and swirled gently for about 20–30 minutes. The filter was removed and similarly washed a second time with 45 mL of 2.0M NaCl (elution buffer) for 20–30 minutes.

Western Blot analysis of PrP$^{sc}$ on the eluate was performed on eluate from the 1.0M NaCl elution buffer and a second Western Blot performed separately on the eluate from the 2.0M NaCl elution, both in accordance with the Western Blot methods of Example 3. With reference to Table 1, data is shown wherein PrP$^{sc}$ is present as having been eluted from the filter after both elutions.

Example 6

Pre Filtration of SBH in 0.22 Micron Filter

In order to determine if the precipitate observed on the filter prior to the depth filtration step of Example 3 contained PrP$^{sc}$, a second run was performed where the SBH spiked SupIII was first pre-filtered through a 0.22 micron filter prior to depth filtration. The materials and procedures of Example 3 were repeated wherein the SBH spiked SupIII was pre-filtered through a 0.22 micron filter prior to depth filtration. With reference to Table 1, it was demonstrated that the pre-filtration removed PrP$^{sc}$ to undetectable levels, indicating that in the prior run the PrP$^{sc}$ was removed by precipitation and mechanical straining, rather than by electrostatic interaction with the depth filter.

Example 7

Elution of PrP$^{sc}$ from Filter

Filter pads used in Example 6 were removed from the filter housing and placed in a petri dish with 45 ml of 1.0M NaCl elution buffer. The petri dish was placed on a rotary shaker and swirled gently for about 20–30 minutes. The filter was removed and similarly washed a second time with 45 mL of 2.0M NaCl elution buffer for 20–30 minutes.

Western Blot analysis of PrP$^{sc}$ on the eluate was performed on eluate from the 1.0M NaCl elution buffer and a second Western Blot performed separately on the eluate from the 2.0M NaCl elution, both in accordance with the Western Blot methods of Example 3.

With reference to Table 1, data is shown wherein PrP$^{sc}$ is present as having been eluted from the filter after both elutions.

Example 8

Clearance of Prions from Blood Sample

Cow whole blood (250 ml) is centrifuged at 100×g to remove the red cells. The resulting plasma is admixed with 75 ml of 22.7% methanol to aggregate the prion material. The admixture is gently swirled for 5 minutes on a rotary mixer. The admixture is passed through a 47 mm Cuno Zeta Plus 90S filter that was prepared as in Example 3 hereinabove. The material is then eluted for Western Blot assay by washing the filter pad in 5 ml of 1.0 M NaCl-15 mg/mL glycine solution. Following extraction and concentration in accordance with Lee et al., 0.5 ml of this material was analyzed by Western Blot in accordance with the methods of Example 3.

The above procedure results in an increase in the detection limit of the assay by greater than 100 fold, now approaching the infectivity assay detection limit. Using current methods available in the art, the infectivity assay can take months to yield results, dependent upon the species under study. These inventors have also shown that the assay can be simplified by detecting the presence of abnormal prion on the membrane surface not requiring G17 elution.

Example 9

Clearance of Prions from Urine Sample

A human urine sample (200 ml) is sedimented for 5 minutes at 3000 rpm to discard occasional cell debris. The urine sample is admixed with 75 ml of 22.7% methanol to aggregate the prion material. The admixture is gently swirled for 5 minutes on a rotary mixer. The admixture is passed through a 47 mm Cuno Zeta Plus 90S filter that was prepared as in Example 3 hereinabove. The material is then eluted for Western Blot assay by washing the filter pad in 5 ml of 1.0 M NaCl -15 mg/mL glycine solution. Following extraction and concentration in accordance with Lee et al., 0.5 ml of this material is analyzed by Western Blot in accordance with the methods of Example 3.

It will be understood by those skilled in the art that the foregoing description and examples are illustrative of practicing the present invention, but are in no way limiting. Variations of the detail presented herein may be made without departing from the scope and spirit of the present invention.

We claim:

1. A method of removing prion protein from a aqueous pharmaceutical composition comprising an IgG anti-D immunoglobulin, wherein the pharmaceutical composition comprises from about 4.0 to 6.0% immunoglobulin by weight, and from about 80 to 200 ppm polysorbate 80, comprising:
   (a) admixing the aqueous composition with from about 2% to about 10% methanol; and
   (b) filtering the admixture of step (a) through a depth filter having a pore size providing a retention of less than about 0.6 microns,
   thereby removing the prion protein, wherein the recovery of the biological protein in its original biological state is substantially maintained at least to a level in excess of about 50%, and wherein the removal of the abnormal infective prion protein may be achieved to an extent of at least about $10^{2.5}$.

* * * * *